United States Patent
Mongrain et al.

(10) Patent No.: US 10,028,847 B2
(45) Date of Patent: Jul. 24, 2018

(54) BIORESORBABLE MEDICAL DEVICES AND METHOD OF MANUFACTURING THE SAME

(71) Applicant: Les Entreprises Nanostent Inc., Montreal (CA)

(72) Inventors: Rosaire Mongrain, Montreal (CA); Olivier Francois Bertrand, Quebec City (CA); Stephen Yue, Montreal (CA)

(73) Assignee: Les Enterprises Nanostent Inc., Quebec (CA)

( * ) Notice: Subject to any disclaimer, the term of this patent is extended or adjusted under 35 U.S.C. 154(b) by 0 days.

(21) Appl. No.: 14/398,521

(22) PCT Filed: May 2, 2013

(86) PCT No.: PCT/CA2013/000445
§ 371 (c)(1),
(2) Date: Nov. 3, 2014

(87) PCT Pub. No.: WO2013/163747
PCT Pub. Date: Nov. 7, 2013

(65) Prior Publication Data
US 2015/0094798 A1  Apr. 2, 2015

Related U.S. Application Data (60) Provisional application No. 61/641,398, filed on May 2, 2012.

(51) Int. Cl.
*A61F 2/82* (2013.01)
*A61L 31/12* (2006.01)
(Continued)

(52) U.S. Cl.
CPC .............. *A61F 2/82* (2013.01); *A61L 31/022* (2013.01); *A61L 31/128* (2013.01);
(Continued)

(58) Field of Classification Search
CPC . A61F 2/82; A61F 2/86; A61L 31/022; A61L 31/148; A61L 31/12; A61L 27/04; A61L 27/042

See application file for complete search history.

(56) References Cited

U.S. PATENT DOCUMENTS

| 6,780,458 B2 * | 8/2004 | Seth ..................... C23C 24/04 427/201 |
| 7,514,122 B2 | 4/2009 | Kramer |

(Continued)

FOREIGN PATENT DOCUMENTS

| CA | 2674195 | 7/2008 |
| CA | 2727568 | 12/2009 |

(Continued)

OTHER PUBLICATIONS

International search report for PCT application PCT/CA2013/000445 filed May 2, 2013, from which the present application is a national phase entry.

(Continued)

*Primary Examiner* — Dinah Baria
(74) *Attorney, Agent, or Firm* — James A. Sheridan; Sheridan Law, LLC (57) ABSTRACT

An intermixed particulate bioresorbable material including cathodic particles and anodic particles bound to each other, wherein the anodic and cathodic particles are made respectively of an anodic and a cathodic material, the anodic and cathodic materials forming a galvanic couple. The anodic and cathodic particles are present in a predetermined ratio and the anodic particles, cathodic particles and predetermined ratio are such that bioresorption of said stent is promoted by galvanic corrosion between said anodic and cathodic materials. Also, a medical device, such as a stent, manufactured using the bioresorbable material and a method (Continued)

of manufacturing the bioresorbable material and the medical device.

28 Claims, 4 Drawing Sheets

(51) Int. Cl.
    *A61L 31/14*     (2006.01)
    *C23C 24/04*     (2006.01)
    *B22F 3/24*     (2006.01)
    *B22F 5/10*     (2006.01)
    *A61L 31/02*     (2006.01)

(52) U.S. Cl.
    CPC .............. *A61L 31/148* (2013.01); *B22F 3/24* (2013.01); *B22F 5/106* (2013.01); *C23C 24/04* (2013.01); *A61F 2210/0004* (2013.01); *A61F 2210/0066* (2013.01); *B22F 2003/247* (2013.01); *B22F 2003/248* (2013.01); *B22F 2998/10* (2013.01)

(56) References Cited

U.S. PATENT DOCUMENTS

| | | | |
|---|---|---|---|
| 7,572,287 B2 * | 8/2009 | Stinson | ............ A61F 2/91 264/235 |
| 7,854,958 B2 | 12/2010 | Kramer | |
| 8,002,821 B2 | 8/2011 | Stinson | |
| 8,080,055 B2 | 12/2011 | Atanasoska et al. | |
| 2006/0112536 A1* | 6/2006 | Herweck | ............ A61F 2/82 29/592 |
| 2007/0219626 A1* | 9/2007 | Rolando | ............ A61F 2/91 623/1.16 |
| 2008/0058919 A1* | 3/2008 | Kramer-Brown | ....... A61L 31/08 623/1.34 |
| 2011/0060419 A1* | 3/2011 | Choi | ............ A61L 27/24 623/23.49 |
| 2012/0101565 A1* | 4/2012 | Stinson | ............ A61F 2/915 623/1.16 |

FOREIGN PATENT DOCUMENTS

| | | |
|---|---|---|
| EP | 1858564 | 11/2007 |
| WO | 2009/158333 | 12/2009 |
| WO | 2010/034098 | 4/2010 |

OTHER PUBLICATIONS

Written opinion for PCT application PCT/CA2013/000445 filed May 2, 2013, from which the present application is a national phase entry.

Supplemental search report for European patent application13784258.9 having a filing date of May 2, 2013 and corresponding to the present application.

* cited by examiner

Mass loss per area vs time curve

FIG 3

Corrosion rate vs time curve

FIG 4

Polarization graph

BIORESORBABLE MEDICAL DEVICES AND METHOD OF MANUFACTURING THE SAME

FIELD OF THE INVENTION

The present invention relates to the art of medical devices. More specifically, the present invention is concerned with bioresorbable medical devices, such as stents for example, and a method of manufacturing the same using cold spray technology. Also, the present invention relates more generally to an intermixed particulate material including particles forming a galvanic couple and to devices manufactured using this material.

BACKGROUND

Obstructive coronary diseases may be caused by a stable or an unstable plaque. An unstable atherosclerotic plaque is vulnerable to rupture and to subsequent thrombogenic reaction, which can lead to sudden death. In general, when the associated stenosis of a stable plaque reaches a certain threshold, it may cause a lack of myocardium perfusion and associated chest pain or angina pectoris.

Historically, the first endovascular mechanical treatment was introduced in 1977 by Andreas Gruentzig who introduced the angioplasty balloon. Percutaneous angioplasty was however associated with a phenomenon called restenosis. Restenosis is essentially the re-obstruction of the vessel caused by vessel recoil, remodeling and hyperplasia. In order to treat the acute recoil and limit the restenosis process, Palmaz-Schatz introduced a new medical implant, the stent, in 1986. A new phenomenon was then observed, in-stent restenosis, or the re-obstruction inside the stent. However, the restenosis rates associated with balloon angioplasty (40-60%) were greatly improved with the advent of stents in 1986 (20-30%) which nevertheless still constitutes a relatively high rate. In order to treat the in-stent restenosis process, Drug Eluting Stents (DES) were introduced. DES were initially coated with antiproliferative and anti-thrombotic compounds. The first DES (Cypher, Cordis) was approved in Europe in 2002. DES initially were effective in limiting restenosis with reported rates between 0 and 16%. However, a few years following their introduction, a serious phenomenon was reported. Late thrombosis (reported by Camenzin on the "Black Sunday" in 2006) was demonstrated to be associated with DES. It was subsequently shown that the rate of late thrombosis continues to increase with time following the implantation. This is phenomenon is of great concern since thrombosis is a life threatening event possibly leading to myocardium infarction.

The causes of late thrombosis are not fully elucidated but processes like chemical compound effect, chronic inflammation and vessel wall injury are reported in the literature. Concerning chronic inflammation and vessel wall injury, a direct link was demonstrated between stent fracture and In-Stent Restenosis (ISR) and thrombosis. ISR is observed both with bare metal stents (BMS) and DES with respective rates of 20-25% and 0-16.7%. The relation with DES fracture was shown to be more frequent than previously thought. The reason is that most of the time stent fracture is clinically silent. However, with imaging modalities, the reported incidence is 1-2% and pathologic investigations reported an incidence of 29% with about 5% associated with adverse effects: inflammation, ulceration, avulsion, ISR, thrombosis.

Furthermore, it was also shown that stent fractures are correlated with anatomical location (tortuosity), with stent fractures more common in the Right Coronary Artery (RCA) with a rate of 57% than in the Left Anterior Descending (LAD) with a rate of 34%, and stent design and lesion types. In addition, stress fractures are also strongly correlated with time: stents may get fully broken over long periods of time. For example, a few broken struts have been reported after implantation times of about 172 d and full stent fracture after implantation times of 1800 d.

This problem is inherently a mechanical problem linked to the notion of fatigue of material. Every material subjected to cyclic loading, such as heart beats, will fatigue and eventually fail. Possible solutions for stent design include developing a superior material for manufacturing the stent for higher longevity and biodegradable stents. Indeed, a biodegradable stent would essentially disappear once it has performed its temporary scaffolding task and thus avoid being subjected to cyclic fatigue.

It is with this perspective that the Igaki-Tamai stent, the first polymeric biodegradable stent made of poly-L-lactide polymer, was introduced in 2003. Since polymers have mechanical properties that are about 2 orders of magnitude lower than metals, mechanical integrity problems were reported, including acute recoil. Given their relative weaker mechanical properties, larger struts are required to ensure proper scaffolding of the vascular wall. The thicker struts, in turn, may cause more resistance to blood flow and may be too large to implant in many blood vessels. Their capacity to properly scaffold plaques with calcification was also mentioned. In addition, larger struts were also associated with more vessel injuries, thus potentially leading to more vessel response and hyperplasia.

At about the same time, biodegradable metallic stents were investigated. The principle was to exploit the property of reactive metals to corrode for biodegradation. The initial selected metal was magnesium. The concept of biodegradation has been shown to work. However, there are several limitations associated with the use of magnesium (WE magnesium). Similar to polymers, magnesium has mechanical properties that are much lower than the current super alloys used for commercial stents (such as 316L stainless steel, L605 cobalt-chromium alloy). As a consequence, thicker struts are also required, and these are associated with the same problems of possible flow disturbances and wall injury. Indeed, negative remodelling was recently demonstrated with the use of the magnesium-based stent.

More recently, other reactive metal alloys were investigated, including iron-manganese alloys and electroformed iron. These alloys have relatively better mechanical strength than magnesium-based alloys. However, the iron-manganese alloys have quite large metallic grains (100 microns), which is an issue given that a stent strut dimension is below 100 microns. Electroformed irons have much smaller grain sizes (2-8 microns) but have limited ductility. Furthermore, control of the degradation rate of these alloys is a challenging task.

Some stents, such as the stent proposed in U.S. Pat. No. 8,080,055 by Atanasoska et al. and issued Dec. 20, 2011, use galvanic corrosion between a core of a stent and a coating made of a different material to promote degradation of the stent in situ. However, such stents require thick struts having a layered structure. This structure also results in heterogeneous degradation as the cathodic layers will remain uncorroded and the anodic layer will also degrade non-homogeneously.

Accordingly, there is a need in the industry to provide an improved bioresorbable stent and other bioresorbable medical devices, along with methods of manufacturing such medical devices. An object of the present invention is therefore to provide such devices and methods.

SUMMARY OF THE INVENTION

In a broad aspect, the invention provides a bioresorbable stent, the bioresorbable stent comprising: a bioresorbable material, the bioresorbable material being an intermixed particulate material including cathodic particles and anodic particles bound to each other. The anodic particles are made of an anodic material and the cathodic particles are made of a cathodic material, the anodic and cathodic materials forming a galvanic couple with the anodic material being electropositive and the cathodic material being electronegative. The anodic and cathodic particles are present in a predetermined ratio in the bioresorbable material. The anodic particles, cathodic particles and predetermined ratio are such that bioresorption of the stent is promoted by galvanic corrosion between the anodic and cathodic materials.

In some embodiments, the cathodic and anodic particles are substantially homogeneously dispersed in the bioresorbable material.

In some embodiments, the anodic and cathodic materials are metallic.

Typically, the anodic and cathodic materials are biocompatible.

In some embodiments, the anodic material is selected from the group consisting of iron, iron alloys and vanadium and the cathodic material is selected from the group consisting of cobalt-chromium alloys, stainless steel, tantalum, titanium and platinum-steels.

In some embodiments, the anodic material and cathodic material are selected from the group of couples consisting of iron/stainless steel and iron/tantalum.

In some embodiments, the anodic and cathodic particles are from about 1 μm to about 30 μm in average size.

In some embodiments, the stent is bioresorbable at a predetermined rate; and the anodic particles, cathodic particles and predetermined ratio are selected such that the stent is bioresorbable at the predetermined rate due to galvanic corrosion between the anodic and cathodic materials.

In some embodiments, the bioresorbable material further includes rate control particles made of a rate control material and dispersed in the bioresorbable material; and the rate control particles affect the galvanic corrosion to change the predetermined rate in accordance with a predetermined rate change.

In some embodiments, the rate control particles increase the predetermined rate. In other embodiments, the rate control particles decrease the predetermined rate. For example, the rate control material is selected from the group consisting of: salts, acids, solid electrolytes, ceramics, dielectrics and metal oxides.

In some embodiments, the bioresorbable material is an annealed material.

In some embodiments, the anodic and cathodic particles include grains of about 1 μm or less in average size. In some embodiments, the anodic and cathodic particles include grains of about 4 μm or less in average size. In some embodiments, the anodic and cathodic particles include grains of about 10 μm or less in average size.

In some embodiments, the anodic and cathodic materials have bulk specific weights that differ by about 50% or less. In some embodiments, the anodic and cathodic materials have bulk specific weights that differ by about 20% or less.

In some embodiments, the anodic and cathodic materials have hardnesses that differ by about 50% or less. In some embodiments, the anodic and cathodic materials have hardnesses that differ by about 20% or less.

In some embodiments, the predetermined ratio is about 4:1 w/w or more in the anodic particles with respect to the cathodic particles. In some embodiments, the predetermined ratio is about 8:1 w/w or more in the anodic particles with respect to the cathodic particles. In some embodiments, the predetermined ratio is about 20:1 w/w or more in the anodic particles with respect to the cathodic particles.

In some embodiments, the cathodic material is stainless steel and the anodic material is iron.

In some embodiments, the bioresorbable material is substantially non-porous. For example, the bioresorbable material has a porosity of about 0.2% or less.

In some embodiments, the stent is entirely made of the bioresorbable material. In other embodiments, the stent further comprises a non-bioresorbable portion.

In another broad aspect, the invention provides a method for manufacturing a bioresorbable stent, the method comprising: providing an anodic powder including anodic particles made of an anodic material; providing a cathodic powder including cathodic particles made of a cathodic material, the anodic and cathodic materials forming a galvanic couple; mixing the anodic and cathodic powders together in a predetermined ratio to obtain a mixed powder; cold spraying the mixed powder on a substrate to obtain a bioresorbable material; and processing the bioresorbable material to form the bioresorbable stent. The anodic particles, cathodic particles and predetermined ratio are selected so that bioresorption of the stent is promoted by galvanic corrosion between the anodic and cathodic materials.

The specific details regarding some embodiments of the stent described hereinabove apply to the present method.

In some embodiments, the method further comprises providing a bioresorption rate control powder including rate control particles made of a rate control material. Mixing the anodic and cathodic powders together includes also mixing a rate control quantity of the bioresorption rate control powder with the anodic and cathodic powders to obtain the mixed powder. The bioresorption rate control powder affects the galvanic corrosion to change the predetermined rate in accordance with a predetermined rate change.

In some embodiments, the substrate is substantially planar.

In some embodiments, processing the bioresorbable material to form the bioresorbable stent includes taking a slice of a predetermined thickness of the bioresorbable material and shaping the slice to form the bioresorbable stent, the slice including substantially opposed slice first and second side edges.

In some embodiments, taking the slice of the predetermined thickness of the bioresorbable material includes cutting the slice with an electrical discharge machine (EDM).

In some embodiments, shaping the slice includes folding the slice to form a cylinder so that the slice first and second side edges are substantially adjacent to each other and welding the slice first and second side edges to each other.

In some embodiments, shaping the slice includes embossing the slice to form a half-cylinder and welding a similar half-cylinder thereto to form a complete cylinder.

In some embodiments, shaping the slice to form the stent includes forming a substantially cylindrical stent blank and cutting out portions of the stent blank to define stent struts.

In some embodiments, cutting out portions of the stent blank includes laser cutting the portions of the stent blank under conditions maintaining the stent blank under an annealing temperature of the anodic and cathodic materials.

In some embodiments, cutting out portions of the stent blank includes laser cutting the portions of the stent blank using a femtosecond laser.

In some embodiments, the method further comprises annealing the bioresorbable material.

In some embodiments, the bioresorbable material is annealed under conditions resulting in grains of the anodic and cathodic materials in the anodic and cathodic particles to remain below about 1 μm in average size. In some embodiments, the bioresorbable material is annealed under conditions resulting in grains of the anodic and cathodic materials in the anodic and cathodic particles to remain below about 4 μm in average size. In some embodiments, the bioresorbable material is annealed under conditions resulting in grains of the anodic and cathodic materials in the anodic and cathodic particles to remain below about 10 μm in average size. In some embodiments, the bioresorbable material is dynamically annealed. In some embodiments, the bioresorbable material is annealed at a temperature between 70% and 90% of a melting temperature of a lowest melting temperature material selected from the anodic and cathodic materials.

In some embodiments, the substrate is substantially planar and processing the bioresorbable material to form the bioresorbable stent includes cutting a cylinder in the bioresorbable material and emptying the cylinder to form a stent blank.

In yet another broad aspect, the invention provides a bioresorbable material, the bioresorbable material being an intermixed particulate material comprising cathodic particles and anodic particles bound to each other. The anodic particles are made of an anodic material and the cathodic particles are made of a cathodic material, the anodic and cathodic materials forming a galvanic couple. The anodic and cathodic particles are present in a predetermined ratio in the bioresorbable material. The anodic particles, cathodic particles and predetermined ratio are such that bioresorption of the bioresorbable material is promoted by galvanic corrosion between the anodic and cathodic materials.

The specific details regarding some embodiments of the stent and the bioresorbable material from which the stent is made as described hereinabove, apply to some embodiments of the present bioresorbable material.

In yet another broad aspect, the invention provides an intermixed particulate material comprising: cathodic particles and anodic particles bound to each other, the anodic particles being made of an anodic material and the cathodic particles being made of a cathodic material, the anodic and cathodic materials forming a galvanic couple.

The specific details regarding some embodiments of the stent and the bioresorbable material from which the stent is made, as described hereinabove, apply to some embodiments of the present particulate material.

In yet another broad aspect, the invention provides a method for manufacturing an intermixed particulate material, the method comprising: providing an anodic powder including anodic particles made of an anodic material; providing a cathodic powder including cathodic particles made of a cathodic material, the anodic and cathodic materials forming a galvanic couple; mixing the anodic and cathodic powders together in a predetermined ratio to obtain a mixed powder; and cold spraying the mixed powder on a substrate to obtain the intermixed particulate material.

The specific details regarding some embodiments of the stent and the bioresorbable material from which the stent is made, as described hereinabove, apply to some embodiments of the present method.

In yet another broad aspect, the invention provides a method for manufacturing a bioresorbable medical device, the method comprising: providing an anodic powder including anodic particles made of an anodic material; providing a cathodic powder including cathodic particles made of a cathodic material, the anodic and cathodic materials forming a galvanic couple; mixing the anodic and cathodic powders together in a predetermined ratio to obtain a mixed powder; cold spraying the mixed powder on a substrate to obtain a bioresorbable material; and processing the bioresorbable material to form the bioresorbable medical device. The anodic particles, cathodic particles and predetermined ratio are such that bioresorption of the stent is promoted by galvanic corrosion between the anodic and cathodic materials.

The specific details regarding some embodiments of the stent and the bioresorbable material from which the stent is made, as described hereinabove, apply to some embodiments of the present method.

In some embodiments, the medical device is selected from the group consisting of stents, markers, anchors, clips, sutures and orthopedic support devices.

In yet another broad aspect, the invention provides a method of implanting a bioresorbable stent in a patient, the method comprising: determining a desired resorption rate of the bioresorbable stent based on the satisfaction of predetermined criteria by the patient; selecting a patient stent from a set of predetermined stents, the predetermined stents being as defined in any one of claims 1 to 28, the patient stent having the desired resorption rate when implanted in the patient; and implanting the patient stent in the patient. In some embodiments, the method further comprises resorbing the stent in the patient at the desired resorption rate.

Advantageously, in some embodiments of the invention, a relatively small bioresorbable stent that is nevertheless strong and ductile enough can be manufactured using the proposed material.

Other objects, advantages and features of the present invention will become more apparent upon reading of the following non-restrictive description of preferred embodiments thereof, given by way of example only and in relation with the following Figures.

DETAILED DESCRIPTION

The present invention relates to a novel material and to bioresorbable medical devices including this material. Also, as detailed hereinbelow, methods of manufacturing the material and medical devices are provided. While the following description mostly refers to a stent manufactured using the proposed material, it is within the scope of the invention to manufacture any suitable medical device using this material, such as, for example, orthopedic devices used as temporary support while tissues heal. Also, while the proposed material is well suited to the manufacture of bioresorbable medical devices, any other medical devices can be manufactured using the proposed material. Finally, while a specific method of manufacturing the proposed medical devices is proposed, in an alternative embodiment of the invention, the medical devices are manufactured using any other suitable method.

Returning to the specific case of a stent, the ideal mechanical properties for stent design are: high Elastic modulus E (to limit stent recoil), low yield strength $S_y$ (to lower balloon pressure for stent expansion), high ultimate strength $S_{UT}$ (for stent longevity), high ductility (for stent longevity and the capacity to withstand deformation under heart pulsation), a high value of the equation $E \cdot t^3$ (for buckling resistance, t being the strut thickness) and the capacity of the stent to withstand $4 \times 10^8$ cycles (fatigue resistance, as per Food and Drug Administration standard ISO 10993).

It is in order to alleviate the limitations mentioned above in the background section that the proposed invention is put forward. The principal objectives were to develop a bioresorbable stent with a new material having a small grain size, the highest possible ductility, high strength and a controllable degradation rate.

Small grain size is advantageous given the size of the stent struts and to avoid a discontinuous material and stress concentration at the interface of grains. It should be noted that grain size should not be confused with particle size, as the proposed material is particulate. The material is made of particles, and the particles each include a plurality of grains. It is also known that for a given material, small grain sizes favor strength and fatigue resistance (basically linked to the Hall-Petch effect: strength $\sim 1/d^{1/2}$ with d the grain size). Apart from increasing strength and fatigue resistance, a smaller grain size has a definite advantage in wear properties. Stents and other medical devices may thus benefit from a significant reduction in grain size. To achieve this result, a cold spray process is proposed to manufacture the novel material.

Indeed, conventional techniques to reduce the grain size, such as cold work, usually make the material too brittle. We propose using the cold gas-dynamic spraying (CGDS) process, referred herein as "cold spray", to generate improved materials with smaller grain sizes. The cold spray process essentially uses the energy stored in a high pressure gas to propel ultra-fine powder (nano-powder) particles at supersonic velocities (300-1500 m/s). The compressed gas is preheated (to a temperature lower than the powder melting temperature) and exits through a nozzle at high velocity. The compressed gas is also fed to a powder feeder which introduces the ultrafine powder in the gas stream jet. The nano-structured powder impacts with a substrate and the particles deform and adhere to form a coating on the substrate. The particles remain relatively cold and retain their submicron to micron range dimensions. No melting is observed and, interestingly, particles flow and mix under very high strain rates generating complex microstructures. Therefore, unwanted effects of high temperatures, such as oxidation, grain growth and thermal stresses, are absent.

The proposed material achieves bioresorption through the use of a mixture of two powders in the manufacturing process. More specifically, the bioresorbable material is an intermixed particulate material comprising cathodic particles and anodic particles bound to each other. The anodic particles are made of an anodic material and the cathodic particles are made of a cathodic material, the anodic and cathodic materials forming a galvanic couple, the anodic material being electropositive relative to the cathodic material, which is therefore electronegative. The anodic and cathodic particles are present in a predetermined ratio in the bioresorbable material. The anodic particles, cathodic particles and predetermined ratio are such that bioresorption of the stent is promoted by galvanic corrosion between the anodic and cathodic materials. Also, conventional passive oxidation of the cathode and anode occurs, which further enhances bioresorption.

It should be noted that the terminology "particles" relates to elements that are smaller than most (or all) of the details of the structure to manufacture. In the case of a stent, the particles have a size that is smaller than the thickness of the stent struts, so that each strut includes many particles. Bioresorption is not achieved by sudden detachment of large elements from the stent, but by gradual disintegration of the stent struts.

It should be noted that this approach is to be contrasted with, for example, the medical devices described in US Patent Application Publication 20100249927 of Yang et al. published on Sep. 30, 2010, in which all the particles have a centre of a first material and a coating of a second material. Such devices are not bioresorbable and the galvanic cells formed are used to generate a current to enhance antiseptic properties of the devices. In these devices, all the particles forming the stent have the same composition. In contrast, the proposed bioresorbable material stent includes two different types of particles. Also, the proposed material and devices manufactured therewith differ greatly from the stents described in U.S. Pat. No. 7,854,958 in the name of Kramer issued Dec. 21, 2010 in which a single material is cold-sprayed to obtain a porous stent. Once again, the devices described in this patent are not bioresorbable. In addition, due to their porous nature, they are relatively fragile.

Also, particulate materials, such as those manufactured using cold spray, are conventionally used to prevent corrosion and wear. As such, only one material is used, often to form a coating on the object to protect. It is contrary to the conventional wisdom in this field to instead promote galvanic corrosion within the material.

The anodic and cathodic particles form a plurality of galvanic cells. The proposed mechanism of bioresorption for the new biodegradable material is similar to the concept of sacrificial anode used in the ship industry to protect boat hulls from corroding, but with the distinction that corrosion of the anode is a desired effect that will lead to loss of cohesion of the proposed material at a desired controlled rate. Two (or more) dissimilar powders are thoroughly mixed prior to the cold spray. Anodic particles (less noble metal) and cathodic particles (more noble metal) are substantially homogeneously mixed using known methods. When in the presence of an electrolyte, current will flow between the anodic and cathodic particles in the cold-sprayed material, which will lead to corrosion of the anodic material, which, in turn, will allow resorption of the medical devices manufactured using the proposed material. In typical embodiments, this resorption will occur substantially homogeneously.

More generally speaking, the invention is an intermixed particulate material comprising cathodic particles and anodic particles bound to each other, the anodic particles being made of an anodic material and the cathodic particles being made of a cathodic material, the anodic and cathodic materials forming a galvanic couple. While bioresorption is a useful property of the proposed material, in alternative embodiments, the proposed material is manufactured such that bioresorption proceeds at such a small rate that it does not occur during the lifetime of the patient. In this case, it is the other properties of the proposed material, such as mechanical properties, that are advantageously used. Typically, when the manufacturing process described hereinbelow is used, the cathodic and anodic particles are randomly and substantially homogeneously dispersed in the bioresorbable material. However, it is possible to have non-random distribution of the anodic and cathodic particles, for example if self-assembling materials are used.

In the case in which a bioresorbable stent is manufactured, the stent includes the bioresorbable material. The stent may be entirely made of the bioresorbable material, or the stent may also include a non-bioresorbable portion made of a non-bioresorbable material, such as pure stainless steel, among other conventional possibilities. In the latter embodiments, a portion of the stent remains in the patient after the remainder of the stent has been resorbed. For example, the non-resorbed portion could include a marker usable to locate the stent implantation site after most of the stent has been resorbed, for example for follow up exams. In another example, the non-resorbed portion could be a stent graft anchoring, a valve anchoring, a clip or a suture that anchors another structure. In these embodiments, the other structure remains in place even after a portion of the stent, which was useful to support the vessel during a healing process, has been resorbed.

When the proposed material is used to manufacture a medical device, the anodic and cathodic materials are biocompatible. Typically, the anodic and cathodic materials are metallic.

In some embodiments of the invention, the anodic material is selected from the group consisting of iron, iron-alloys and vanadium, and the cathodic material is selected from the group consisting of cobalt-chromium alloys, stainless steel, tantalum, titanium and platinum-steels. In more specific embodiments of the invention, the anodic material and cathodic material are selected from the group of couples consisting of iron/stainless steel and iron-tantalum. However, other possibilities are within the scope of the invention.

The anodic and cathodic particles are in some embodiments from about 1 μm to about 30 μm in average size, which is advantageous in the manufacture of devices including sub-millimeter sized elements. Average size is defined as a mean value in a Gaussian distribution of sizes, as assessed using microscope imaging. For example, the anodic and cathodic particles are produced by melting the anodic and cathodic materials and pouring the molten materials on a spinning wheel, which creates a rain of small droplets of molten material. Cold water is sprayed afterward on the resulting droplets, which solidifies the anodic and cathodic particles. The resulting shape is substantially spherical and size refers to the diameter of the particles. In another example, the anodic and cathodic particles are created by grinding the anodic and cathodic materials in bulk form to make powders. The resulting particles are irregular. These irregular particles are then heated, which again produces substantially spherical anodic and cathodic particles, and size refers again to the diameter of the particles.

The anodic and cathodic particles each include grains. The grains typically have much smaller dimensions than the particles. In some embodiments of the invention, the grains are about 1 μm or less in average size. In other embodiments, the grains are about 4 μm or less in average size. In yet other embodiments, the grains are about 10 μm or less in average size. Relatively small grain size promotes ductility of the devices manufactured using the proposed devices, which is often advantageous.

When a cold spray process is used, it is useful in some embodiments to have anodic and cathodic particles with some properties that are similar to promote good material properties. For example, the anodic and cathodic materials have bulk specific weights that differ by about 50% or less, and in more specific examples, the anodic and cathodic materials have bulk specific weights that differ by about 20% or less. This promotes good mixing of the particles to ensure homogeneous and random distribution of the anodic and cathodic particles in the proposed material. The bulk specific weight refers to the specific weight of the material in bulk form, not to the specific weight of the material in particulate powder form. In the context of this document, "differing by X %" is to be interpreted as meaning that the largest property is X % larger than the smallest property. For example, a material having a specific weight of 2 $g/cm^3$ and a material having a specific weight of 3 $g/cm^3$ differ in specific weight by 50%.

In some embodiments of the invention, the anodic and cathodic materials have hardnesses that differ by about 50% or less, and in more specific examples, the anodic and cathodic materials have hardnesses that differ by about 20% or less. This promotes good adhesion between the particles.

One could hypothesize that a ratio of 1:1 w/w between the number of cathodic and anodic particles would be desired so that the same number of electron receiving and releasing particles are provided. While this ratio can provide bioresorbable materials, it was found that, surprisingly, a predetermined ratio of about 4:1 w/w or more in the anodic particles with respect to the cathodic particles provides faster corrosion, which is advantageous in some situations. It is believed that in more extreme examples, a predetermined ratio of about 8:1 w/w or more in the anodic particles with respect to the cathodic particles, or even a predetermined ratio of about 20:1 w/w or more in the anodic particles with respect to the cathodic particles is also achievable while preserving the bioresorption properties.

In some embodiments, the proposed material is a dynamically annealed material in which the material has been heated at a time varying temperature to correct defects within the particles without promoting large grain growth. This preserves ductility while increasing hardness. However, other types of annealing are possible to achieve suitable grain size.

In addition to manipulation of the many variables involved in the structure of the proposed material, such as selection of anodic and cathodic materials and their proportions, dimensions of particles, manufacturing conditions and annealing conditions, in some embodiments additional particles are present in the material to control bioresorption rates.

More specifically, the medical device manufactured, such as a stent, is bioresorbable at a predetermined rate. To that effect, the anodic particles, cathodic particles and predetermined ratio between the two are selected such that the stent is bioresorbable at the predetermined rate due to galvanic corrosion between the anodic and cathodic materials. To guide the selection of particles, galvanic corrosion theories that relate the current density between two dissimilar materials and their degradation rates may be used. In those theoretical descriptions, an equation for galvanic corrosion is derived based on the corrosion current density of uncoupled alloys. This allows the quantification of the corrosion rates based on potentiodynamic current measurements and permits an estimate of the mass depletion rates based on these current measurements. Examples of such theories are found in "Electrochemical Theory of Galvanic Corrosion", John W. Oldfield, ASTM STP 978H. P. Hack Ed American Society for Testing and Materials, Philadelphia, 1988, p. 5-22 and "A Theoretical approach to galvanic corrosion, allowing for cathode dissolution", S. Fangteng, E. A. Charles, Corrosion Science 28(7):649-655, 1988. These two documents are hereby incorporated by reference in their entirety.

In some embodiments of the invention, the bioresorbable material further includes rate control particles made of a rate control material and dispersed in the bioresorbable material. The rate control particles affect the galvanic corrosion to change the predetermined rate in accordance with a predetermined rate change. For example, the rate control particles increase the predetermined rate by increasing electron transport between the anodic and cathodic particles. In another example, the rate control particles decrease the predetermined rate by decreasing electron transport between the anodic and cathodic particles. Specific examples of rate control particles that increase the predetermined rate include salts (such as calcium, potassium and sodium salts), acids and solid electrolytes. Specific examples of rate control particles that decrease the predetermined rate include ceramics, dielectrics and oxides.

Typically, the proposed material is substantially non-porous. For example, this is achieved by having a material that has a porosity of about 0.2% or less.

Figure 1:
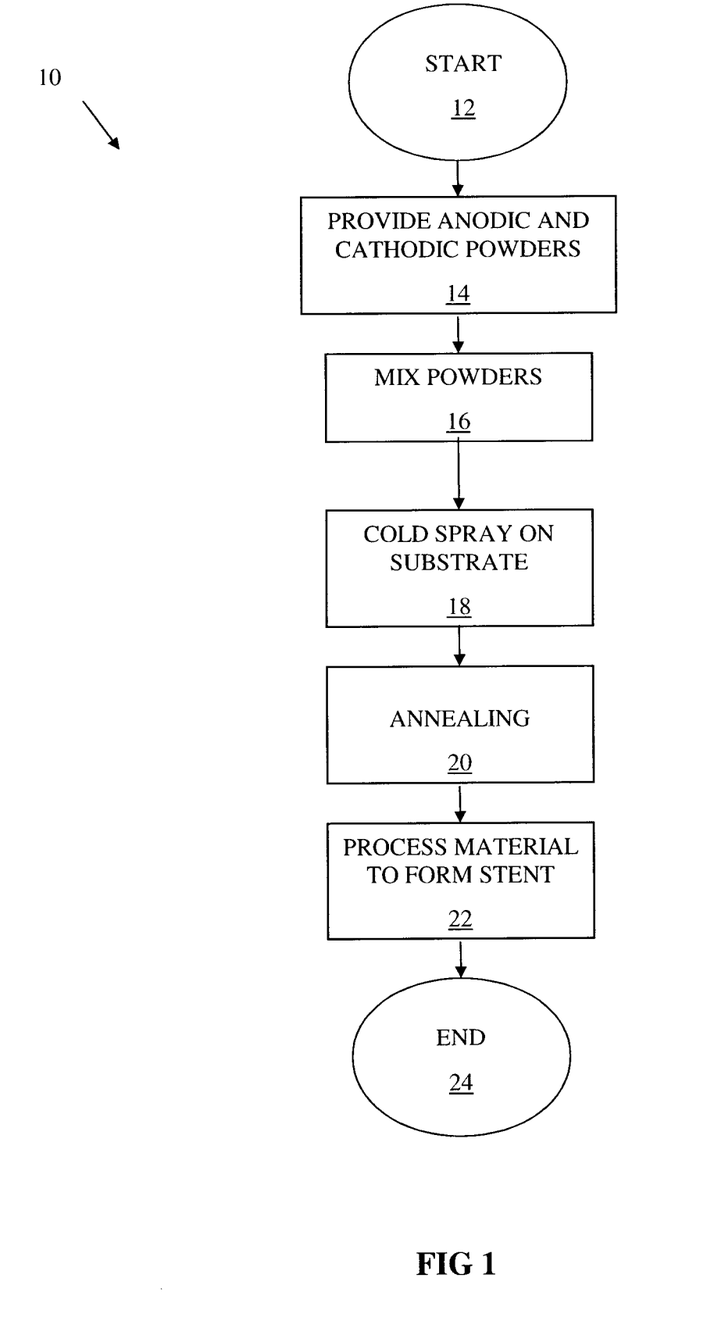
FIG. 1, in a flow chart, illustrates a method for manufacturing a stent in accordance with an embodiment of the present invention.

An example of a manner of manufacturing a stent is given hereinbelow with reference to FIG. 1. However, other devices can be similarly manufactured using the proposed material. More specifically, FIG. 1 illustrates a method 10 for manufacturing a bioresorbable stent. The method begins at step 12. Then, at step 14, an anodic powder including anodic particles made of an anodic material and a cathodic powder including cathodic particles made of a cathodic material are provided. The anodic and cathodic materials form a galvanic couple, as described in greater detail hereinabove. Then, at step 16, the method includes mixing the anodic and cathodic powders together in the predetermined ratio to obtain a mixed powder. Afterward, at step 18, the method includes cold spraying the mixed powder on a substrate, for example a steel substrate, to obtain a bioresorbable material. In some embodiments of the invention, the substrate is substantially planar, but other shapes are possible. In some embodiments of the invention, at step 20, the material is annealed. In both cases, whether there is annealing or not, the method then proceeds to step 22 of processing the bioresorbable material to form the bioresorbable stent and ends at step 24. When it is desired to manufacture the material only for future use, step 22 is omitted from the method 10. The proposed bioresorbable materials manufactured are complex multi-scale structures (nano-size grains, micro-size particles, and macro-size layering). Dedicated thermal treatment, annealing, retains the multi-scale structure while improving the ductility for stent usage.

In some embodiments of the invention, step 14 also includes providing a bioresorption rate control powder including rate control particles made of the rate control material. In these embodiments, step 16 also includes mixing a rate control quantity of the bioresorption rate control powder with the anodic and cathodic powders to obtain the mixed powder.

Step 22 may be performed in many possible manners. A non-exclusive but advantageous manner of performing step 22 is to first take a slice of a predetermined thickness of the bioresorbable material and then shape the slice to form the bioresorbable stent. The slice includes substantially opposed slice first and second side edges extending between substantially opposed ends of the slice. The thickness of the slice is about the thickness of the stent after it has been manufactured. For example, taking the slice of the predetermined thickness of the bioresorbable material includes cutting the slice with an electrical discharge machine (EDM). It has been found that slices of less than 100 µm in predetermined thickness are obtainable, which allows manufacturing relatively small stents.

In a first example, shaping the slice includes folding the slice to form a cylinder so that the slice first and second side edges are substantially adjacent to each other and welding the slice first and second side edges to each other. In a second example, shaping the slice includes embossing the slice to form a half-cylinder and welding a similar half-cylinder thereto to form a complete cylinder.

Typically, shaping the slice to form the stent includes forming a substantially cylindrical stent blank and cutting out portions of the stent blank to define stent struts. Typically, cutting out portions of the stent blank includes laser cutting the portions of the stent blank under conditions maintaining the stent blank under an annealing temperature of the anodic and cathodic materials, for example using a so-called "cold" laser, or femtosecond laser. However, in alternative embodiments, the portions of the flat material are first cut out and the resulting flattened stent is then folded in a cylindrical shape.

In another variant, step 22 is performed using a relatively thicker bioresorbable material and processing the bioresorbable material to form the bioresorbable stent includes cutting a cylinder in the bioresorbable material and emptying the cylinder to form the stent blank. This variant advantageously removes the need for welding.

After the above steps, conventional stent manufacturing steps are performed, such as crimping the stent on a balloon for implantation.

Annealing is typically performed before manufacturing the stent, but in alternative embodiments of the invention, it is performed after manufacturing the stent or on the stent blank, among other possibilities. For example, when the anodic and cathodic materials are respectively iron and stainless steel, annealing is performed by heating the material between 800 and 1100° C. for a duration of 30 to 120 minutes. More generally, annealing is performed typically at a temperature of between 70 and 90% of the melting temperature of the component material of the stent (anodic and cathodic materials) having the lowest melting temperature.

To use the stent in a patient, first, a desired resorption rate of the bioresorbable stent based on the satisfaction of predetermined criteria by the patient is determined. This determination depends on clinical and biological criteria. Then, the method of use includes selecting a patient stent from a set of predetermined stents, the patient stent having the desired resorption rate when implanted in the patient. Afterward, the patient stent is implanted in the patient. The proposed stent has been found to be advantageous for use in coronary and pulmonary blood vessels, but other uses are possible. For example, the proposed stent is usable in hepatic, biliary, and peripheral vessels. Also, the proposed stent is usable in non-blood carrying vessels. Finally, the method further comprises resorbing the stent in the patient at the desired resorption rate.

The ductility of the cold sprayed bioresorbable material typically needs to be improved with thermal treatment. Various treatments are possible to optimize the final desired mechanical properties. After cold spraying, the bioresorbable material is in a highly work-hardened state. Annealing is usually performed to restore the structure to a re-crystallized state, which is often preferable for various mechanical properties. Furthermore, control of annealing enables control of mechanical properties. Annealing can be performed isothermally by heating the material, for example in an electric resistance furnace in air followed by air cooling. However, one has to ensure that the thermal treatment preserves the micro and the nano structures of the sprayed materials.

EXAMPLE

Figure 2A:
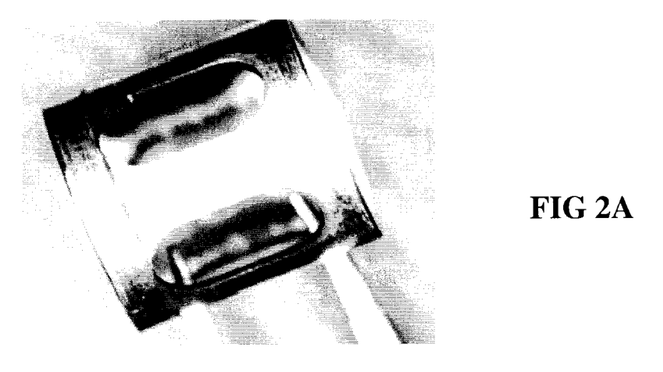
FIGS. 2A to 2C, in photographs, illustrate a stent manufactured using the method of FIG. 1.
Figure 2B:
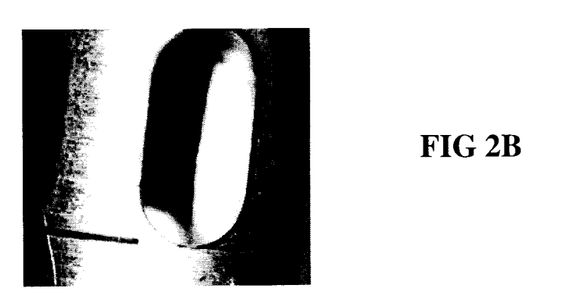
Figure 2C:
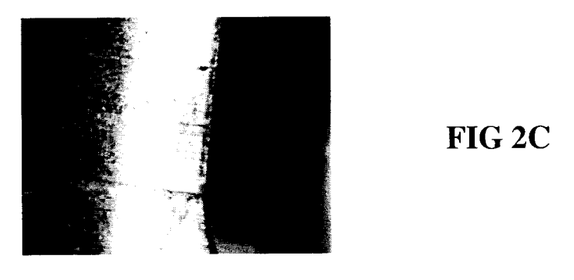
Figure 6:
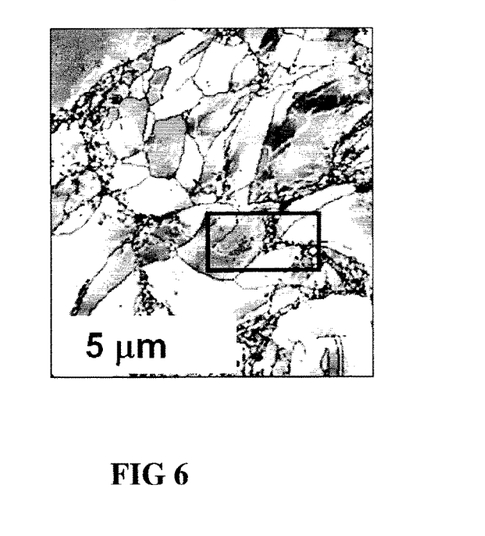
FIG. 6, in an Electron BackScatter Diffraction (EBSD) Euler angle map, illustrates the microstructure of the material used to manufacture the stent of FIG. 2.

FIGS. 2A to 2C illustrate at various scales a stent manufactured using the method 10. This stent is made of cold sprayed iron particles and stainless steel particles, both having an average size of about 5 μm, in a 4:1 w/w ratio and has an outer diameter of 8 mm with 200 μm thick struts. No annealing was performed. FIG. 6 illustrates the microstructure of the material used to manufacture the stent, after the cold spraying step.

Figure 3:
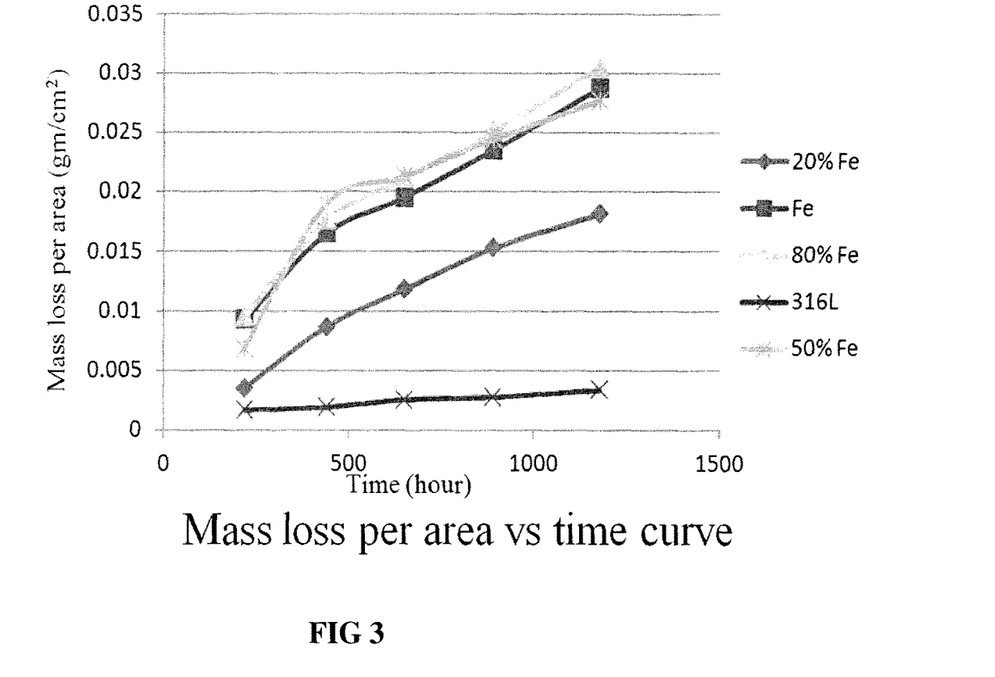
FIG. 3, in an X-Y graph, illustrates mass loss per unit area for iron/stainless steel samples made in accordance with the method of FIG. 1 for pure iron (FE), pure stainless steel (316L alloy) and various mixtures of iron and stainless steel.
Figure 4:
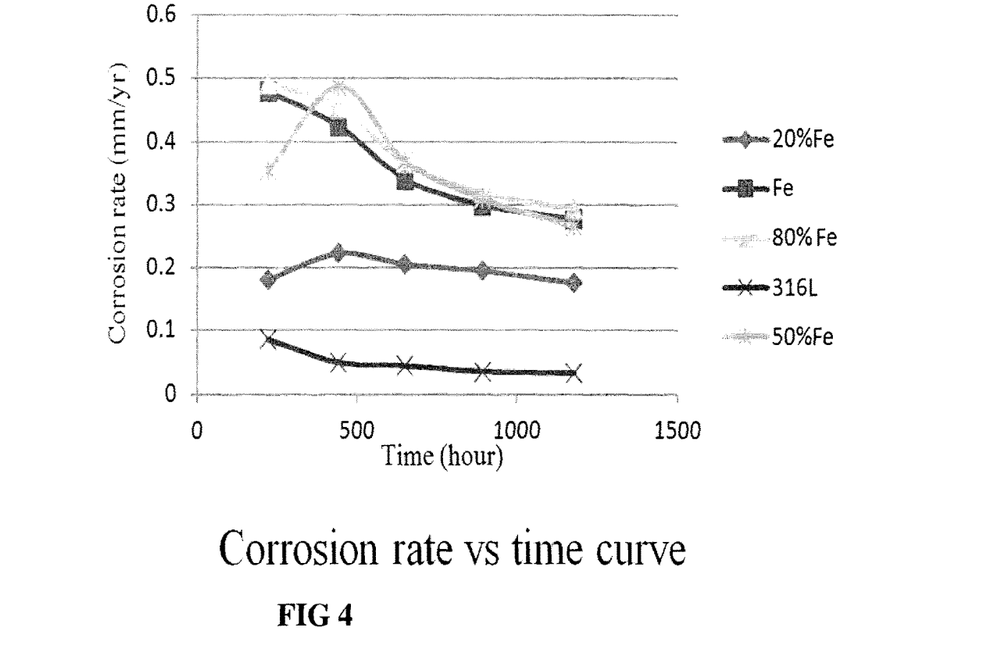
FIG. 4, in an X-Y graph, illustrates corrosion rate obtained from the data shown in FIG. 3.
Figure 5:
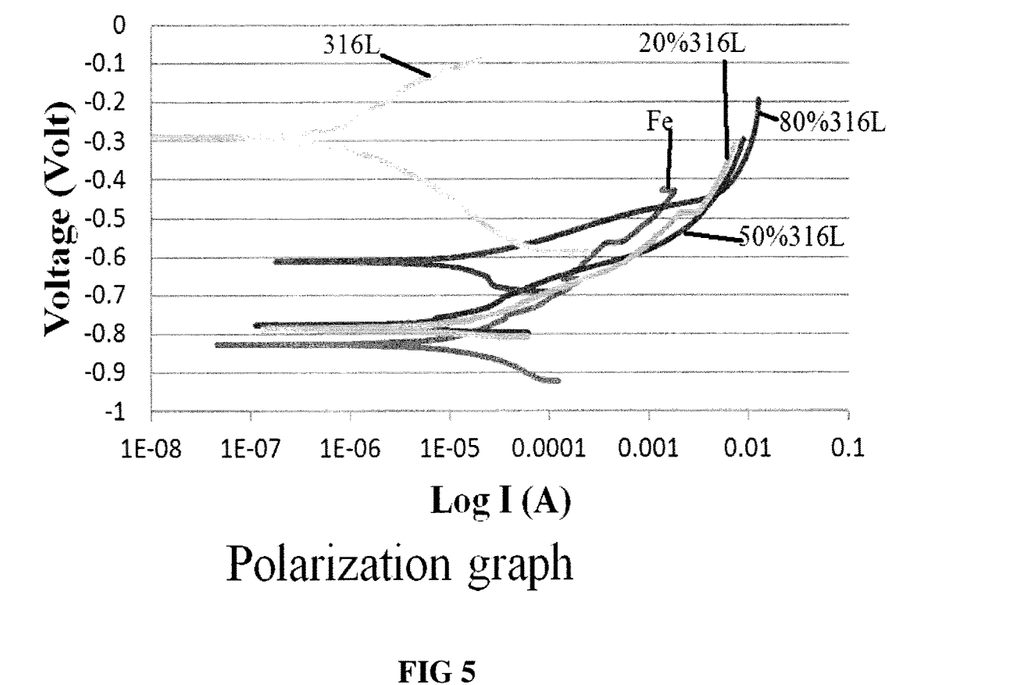
FIG. 5, in an X-Y graph, illustrates polarization curves used to determine in an alternative manner the corrosion rate for the samples used to obtain the data presented in FIGS. 3 and 4.

FIG. 3 illustrates corrosion rate of various bioresorbable materials manufactured using the method 10, without step 22. The particles were iron and stainless steel (316L). Curves of corrosion as a function of time per unit area are shown for the various proportions. FIG. 4 shows this data in a different form where the corrosion rate is plotted. Finally, FIG. 5 illustrates the polarization graphs used to investigate corrosion rate in an alternative manner. The corrosion rates were 0.215 mm/yr for pure iron, 0.18 mm/yr for 316L/iron in a 1:4 ratio, 0.1128 mm/yr for 316L/iron in a 1:1 ratio, and 0.107 mm/yr for 316L/iron in a 4:1 ratio.

Although the present invention has been described hereinabove by way of preferred embodiments thereof, it can be modified, without departing from the spirit and nature of the subject invention as defined in the appended claims.

What is claimed is:

1. A bioresorbable stent, said bioresorbable stent consisting of: a bioresorbable material, said bioresorbable material being an intermixed particulate material consisting of cathodic particles and anodic particles bound to each other, wherein said anodic particles are made of an anodic material and said cathodic particles are made of a cathodic material, said anodic and cathodic materials forming a galvanic couple with said anodic material being electropositive and said cathodic material being electronegative;

said anodic and cathodic particles are present in a predetermined ratio in said bioresorbable material;

said anodic particles, cathodic particles and predetermined ratio are such that bioresorption of said stent is promoted by galvanic corrosion between said anodic and cathodic materials;

said stent being entirely made of said bioresorbable material, said bioresorbable material is a cold sprayed particles material, and said bioresorbable stent is formed by a method comprising:

mixing said anodic and cathodic particles together in said predetermined ratio to obtain a mixed powder, cold spraying said mixed powder on a substrate to obtain said bioresorbable material, and processing the bioresorbable material to form said bioresorbable stent by removing the substrate.

2. A stent as defined in claim 1, wherein said cathodic and anodic particles are substantially homogeneously dispersed in said bioresorbable material.

3. A stent as defined in claim 1, wherein said anodic and cathodic materials are metallic.

4. A stent as defined in claim 1, wherein said anodic and cathodic materials are biocompatible.

5. A stent as defined in claim 1, wherein said anodic material is selected from the group consisting of iron, iron alloys and vanadium and said cathodic material is selected from the group consisting of cobalt-chromium alloys, stainless steel, tantalum, titanium and platinum-steels.

6. A stent as defined in claim 1, wherein said anodic material and cathodic material are selected from the group of couples consisting of iron/stainless steel and iron/tantalum.

7. A stent as defined in claim 1, wherein said anodic and cathodic particles are from 1 μm to 30 μm in average size.

8. A stent as defined in claim 1, wherein said stent is bioresorbable at a predetermined rate; and said anodic particles, cathodic particles and predetermined ratio are selected such that said stent is bioresorbable at said predetermined rate due to galvanic corrosion between said anodic and cathodic materials.

9. A stent as defined in claim 1, wherein said bioresorbable material is an annealed material.

10. A stent as defined in claim 1, wherein said anodic and cathodic particles include grains of 1 μm or less in average size.

11. A stent as defined in claim 1, wherein said anodic and cathodic particles include grains of 4 μm or less in average size.

12. A stent as defined in claim 1, wherein said anodic and cathodic particles include grains of 10 μm or less in average size.

13. A stent as defined in claim 1, wherein said anodic and cathodic materials have bulk specific weights that differ by 50% or less.

14. A stent as defined in claim 1, wherein said anodic and cathodic materials have bulk specific weights that differ by 20% or less.

15. A stent as defined in claim 1, wherein said anodic and cathodic materials have hardnesses that differ by 50% or less.

16. A stent as defined in claim 1, wherein said anodic and cathodic materials have hardnesses that differ by 20% or less.

17. A stent as defined in claim 1, wherein said predetermined ratio is 4:1 w/w or more in said anodic particles with respect to said cathodic particles.

18. A stent as defined in claim 1, wherein said predetermined ratio is 8:1 w/w or more in said anodic particles with respect to said cathodic particles.

19. A stent as defined in claim 1, wherein said predetermined ratio is 20:1 w/w or more in said anodic particles with respect to said cathodic particles.

20. A stent as defined in claim 1, wherein said cathodic material is stainless steel and said anodic material is iron.

21. A stent as defined in claim 1, wherein said bioresorbable material is substantially non-porous.

22. A stent as defined in claim 21, wherein said bioresorbable material has a porosity of 0.2% or less.

23. The bioresorbable stent as defined in claim 1, wherein said substrate is substantially planar and wherein processing said bioresorbable material to form said bioresorbable stent includes taking a slice of a predetermined thickness of said bioresorbable material and shaping said slice to form said bioresorbable stent, said slice including substantially opposed slice first and second side edges.

24. The bioresorbable stent as defined in claim 23, wherein shaping said slice includes folding said slice to form a cylinder so that said slice first and second side edges are substantially adjacent to each other and welding said slice first and second side edges to each other.

25. The bioresorbable stent as defined in claim 23, wherein shaping said slice includes embossing said slice to form a half-cylinder and welding a similar half-cylinder thereto to form a complete cylinder.

26. The bioresorbable stent as defined in claim 23, wherein shaping said slice to form said stent includes forming a substantially cylindrical stent blank and cutting out portions of said stent blank to define stent struts.

27. The bioresorbable stent as defined in claim 1, wherein the method further comprises annealing said bioresorbable material.

28. The bioresorbable stent as defined in claim 1, wherein said substrate is substantially planar; and wherein processing said bioresorbable material to form said bioresorbable stent includes cutting a cylinder in said bioresorbable material and emptying said cylinder to form a stent blank.

* * * * *